US012746275B2

(12) United States Patent
Patel et al.

(10) Patent No.: US 12,746,275 B2
(45) Date of Patent: Sep. 29, 2026

(54) IMPLANTS FOR RELEASE OF LIPOPHILIC OR AMPHIPHILIC PHARMACEUTICAL SUBSTANCES

(71) Applicant: ReacX Pharmaceuticals, Inc., South San Francisco, CA (US)

(72) Inventors: Rajesh A. Patel, Redwood City, CA (US); Sunil Sreedharan, South San Francisco, CA (US); Benjamin Furman, San Antonio, TX (US)

(73) Assignee: ReacX Pharmaceuticals, Inc., South San Francisco, CA (US)

( * ) Notice: Subject to any disclaimer, the term of this patent is extended or adjusted under 35 U.S.C. 154(b) by 388 days.

(21) Appl. No.: 17/253,078

(22) PCT Filed: Jun. 25, 2019

(86) PCT No.: PCT/US2019/039072
§ 371 (c)(1),
(2) Date: Dec. 16, 2020

(87) PCT Pub. No.: WO2020/006000
PCT Pub. Date: Jan. 2, 2020

(65) Prior Publication Data

US 2021/0113664 A1 Apr. 22, 2021

Related U.S. Application Data

(60) Provisional application No. 62/689,735, filed on Jun. 25, 2018.

(51) Int. Cl.
*A61K 9/00* (2006.01)
*A61K 9/14* (2006.01)
(Continued)

(52) U.S. Cl.
CPC ............ *A61K 38/26* (2013.01); *A61K 9/0024* (2013.01); *A61K 9/145* (2013.01); *A61K 9/146* (2013.01); *A61K 47/32* (2013.01)

(58) Field of Classification Search
None
See application file for complete search history.

(56) References Cited

U.S. PATENT DOCUMENTS 5,626,862 A * 5/1997 Brem .................. A61K 9/2031 424/1.11
5,633,000 A 5/1997 Grossman et al.
(Continued)

FOREIGN PATENT DOCUMENTS

CN 102639184 A * 8/2012 ............ A61M 37/00
WO 2017/068351 A1 4/2017

OTHER PUBLICATIONS

Xi Liu et al. "Evaluation of two polymeric blends (EVA/PLA and EVA/PEG) as coating film materials for paclitaxel-eluting stent application." Journal of Materials Science: Materials in Medicine, vol. 22, 2011, pp. 327-337. (Year: 2011).*
(Continued)

*Primary Examiner* — Isaac Shomer
(74) *Attorney, Agent, or Firm* — Wiggin and Dana LLP

(57) ABSTRACT

Implants are described which comprise lipophilic pharmaceutical substances. Excipients are used which provide appropriate and controllable/tunable release of the lipophilic drug from the matrix of the implant. The implants can be implanted into a patient for release of the pharmaceutical substances. Methods of making and using such implants are also described.

38 Claims, 1 Drawing Sheet

(51) Int. Cl.
*A61K 38/26* (2006.01)
*A61K 47/32* (2006.01)

(56) References Cited

U.S. PATENT DOCUMENTS

| | | | | | |
|---|---|---|---|---|---|
| 5,851,547 | A * | 12/1998 | Fujioka | A61K 9/0092 | 424/424 |
| 8,291,910 | B2 * | 10/2012 | de Graaff | A61F 6/18 | 128/833 |
| 9,345,686 | B2 | 5/2016 | De Graaff et al. | | |
| 2003/0082234 | A1 * | 5/2003 | Seo | A61K 47/34 | 424/85.2 |
| 2003/0224059 | A1 * | 12/2003 | Lerner | A61K 9/1682 | 514/217 |
| 2007/0026046 | A1 | 2/2007 | Fogg et al. | | |
| 2007/0160639 | A1 * | 7/2007 | Pantelidis | A61L 31/16 | 514/291 |
| 2008/0020016 | A1 | 1/2008 | Li et al. | | |
| 2009/0060970 | A1 * | 3/2009 | Toner | A61L 31/16 | 514/56 |
| 2009/0246245 | A1 * | 10/2009 | Mauriac | A61K 9/0024 | 264/176.1 |
| 2009/0264385 | A1 * | 10/2009 | Crowley | A61K 9/006 | 514/315 |
| 2010/0124565 | A1 * | 5/2010 | Spada | A61P 27/02 | 514/249 |
| 2011/0059140 | A1 * | 3/2011 | Winter | A61K 9/0024 | 424/94.61 |
| 2011/0190688 | A1 * | 8/2011 | Tagliaferri | A61M 37/00 | 604/20 |
| 2012/0034306 | A1 * | 2/2012 | Pollock | A61P 25/04 | 514/282 |
| 2012/0283624 | A1 * | 11/2012 | Shirley | A61M 25/104 | 604/22 |
| 2013/0252894 | A1 * | 9/2013 | Kuzma | A61P 3/10 | 514/11.7 |
| 2017/0273901 | A1 | 9/2017 | Fu et al. | | |
| 2018/0127359 | A1 | 5/2018 | Fung et al. | | |
| 2019/0133951 | A1 | 5/2019 | Liu et al. | | |

OTHER PUBLICATIONS

Andreas Niethammer, Gerhard Gaedicke, Holger N. Lode, and Wolfgang Wrasidlo. "Synthesis and Preclinical Characterization of a Paclitaxel Prodrug with Improved Antitumor Activity and Water Solubility." Bioconjugate Chemistry, vol. 12, 2001, pp. 414-420. (Year: 2001).*

Christian Schneider, Robert Langer, Donald Loveday, Dirk Haire. "Applications of ethylene vinyl acetate copolymers (EVA) in drug delivery systems." Journal of Controlled Release, vol. 262, 2017, pp. 284-295. (Year: 2017).*

Christian Schneider,, Robert Langer, Donald Loveday, Dirk Hair. "Applications of ethylene vinyl acetate copolymers (EVA) in drug delivery systems." Journal of Controlled Release 262 (2017) 284-295. (Year: 2017).*

Vishal Gupta. "Glucagon-like peptide-1 analogues: An overview." Indian Journal of Endocrinology and Metabolism, May-Jun. 2013, vol. 17, Issue 3, pp. 413-421. (Year: 2013).*

JN Israelachvili, S Marcelja, and RG Horn. "Physical principles of membrane organization." Quarterly Reviews of Biophysics 13, 2 (1980), pp. 121-200. (Year: 1980).*

English Translation of CN 102639184 A. Originally published in Chinese on Aug. 15, 2012, translation obtained by examiner on Jun. 24, 2024, 7 printed pages. (Year: 2012).*

Lundberg, B.B. et al. "A lipophilic paclitaxel derivative incorporated in a lipid emulsion for parenteral administration," 2003, 86, pp. 93-100.

International Search Report, PCT/US2019/039072, mailed Sep. 13, 2019.

European Search Report, EP 19 82 7051.4, mailed Feb. 24, 2022.

* cited by examiner

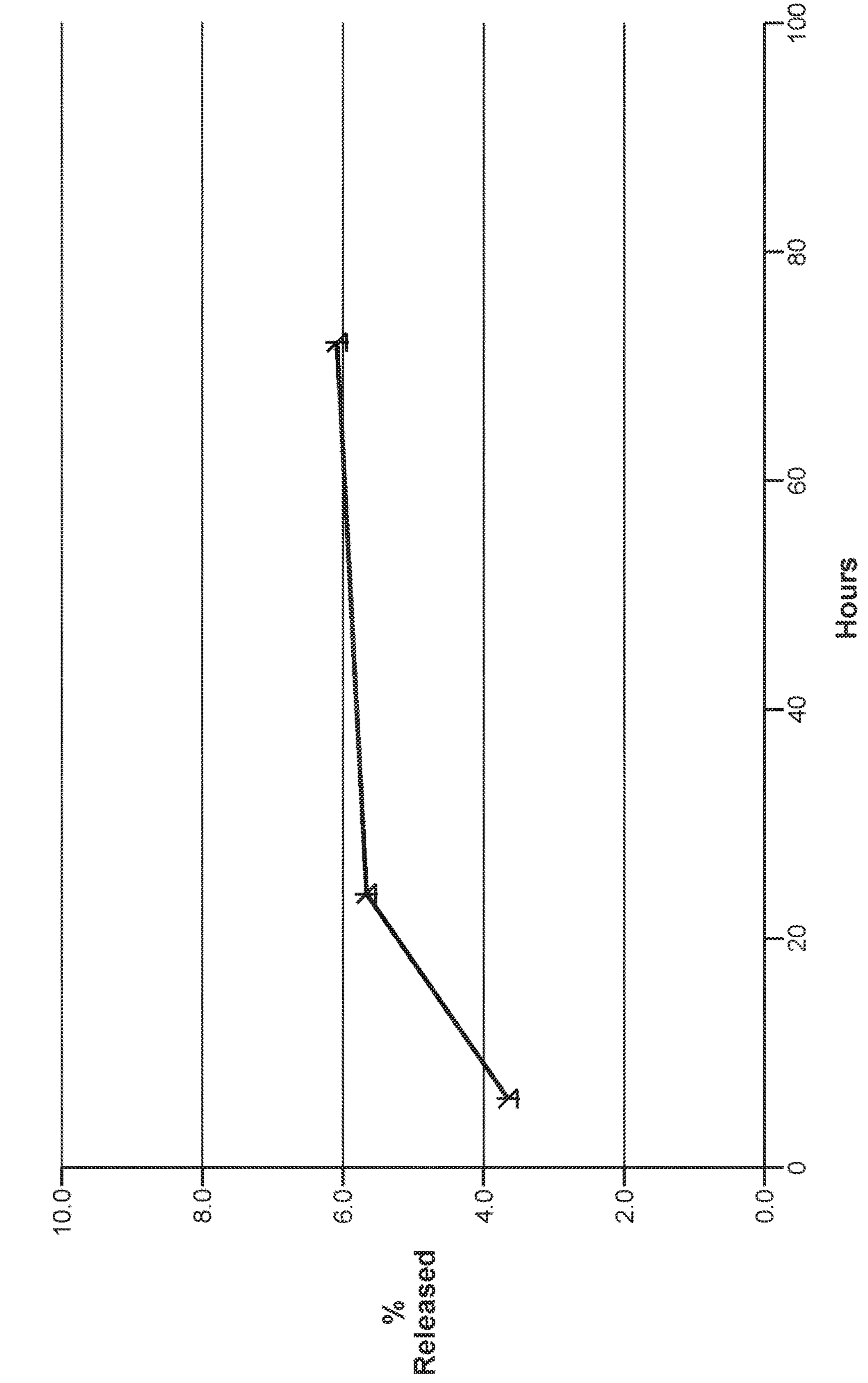
% Released
10.0
8.0
6.0
4.0
2.0
0.0
0
20
40
60
80
100
Hours

IMPLANTS FOR RELEASE OF LIPOPHILIC OR AMPHIPHILIC PHARMACEUTICAL SUBSTANCES

CROSS REFERENCE TO RELATED APPLICATIONS

This application is a national phase filing under 35 U.S.C. § 371 of International Application No. PCT/US2019/039072, filed internationally on Jun. 25, 2019, which claims priority benefit of U.S. Provisional Patent Application No. 62/689,735, filed Jun. 25, 2018. The entire contents of that those applications are hereby incorporated by reference herein.

TECHNICAL FIELD

Provided are implants which comprise lipophilic or amphiphilic pharmaceutical substances which can be implanted into a patient for release of the pharmaceutical substances, as well as methods of making and using such structures.

BACKGROUND OF THE INVENTION

Many patients require long-term, regular dosing with drugs or pharmaceutical substances. Several problems can arise during long-term administration of drugs taken orally or by other routes requiring frequent administration. Compliance with an extended dosing regimen can often be inconvenient or difficult. For example, patients with impaired cognitive function (due to Alzheimer's disease or other disorders) may not be able to self-administer drugs reliably, requiring a caregiver to ensure that medications are taken properly. Furthermore, enteral drug delivery is sometimes poorly tolerated or prohibited in patients with particular indications. Frequent or periodic administration, such as would occur with daily oral and sublingual delivery, can result in blood concentrations of drug peaking quickly after initial administration, then dropping steeply before the next administration. Intravenous drug delivery requires trained personnel for administration, and is impractical for prolonged outpatient treatment.

Implants used for drug delivery can overcome several problems with oral, sublingual, or intravenous administration of drugs. These implantable devices can produce long-term, continuous delivery of drugs, ensure compliance independent of the patient, maintain stable blood levels of medication, and reduce the likelihood of accidental use, abuse, or diversion for sale. Continuous release of a compound in vivo over an extended duration may be achieved via implantation of a device containing the compound encapsulated in a polymeric matrix. Examples of implantable polymeric devices for continuous drug release are described in, e.g., U.S. Pat. Nos. 4,883,666; 5,114,719; and 5,601,835. Patel et al. U.S. Pat. No. 7,736,665, U.S. Patent Application Publication Nos. 2004/0033250, 2007/0275031, and 2008/0026031, and Kleppner et al. 2006 J. Pharm. Pharmacol. 58:295-302 describe an implantable device comprising buprenorphine blended with ethylene vinyl acetate (EVA copolymer). Patel et al. U.S. Patent Application Publication No. 2005/0031668 describes an implantable polymeric device for sustained release of nalmefene. Patel et al. U.S. Patent Application Publication No. 2005/0031667 describes an implantable polymeric device for sustained release of dopamine agonists. Additional drug delivery devices include stents coated with compositions comprising drugs. Various devices and coatings are described in U.S. Pat. No. 6,506,437 to Harish; U.S. Pat. No. 7,364,748 to Claude; and U.S. Pat. No. 7,384,660 to Hossainy. U.S. Pat. No. 3,625,214 describes a drug-delivery device for prolonged drug delivery, fabricated in a spiral or "jellyroll" fashion. U.S. Pat. No. 3,926,188 describes a three-layer laminate drug dispenser comprising a core lamina of a crystalline drug of low water solubility dispersed in a polymer matrix, interposed between outer laminas made of a drug release rate controlling polymer. U.S. Pat. No. 5,683,719 describes a controlled release composition comprising an extruded core of active material and excipients, the core being coated in a water insoluble coating.

However, certain drugs do not release well from an implant. In particular, lipophilic drugs and amphiphilic drugs may interact strongly with the material from which the implant is fabricated, and will elute poorly or not at all from the implant. Implants are disclosed herein which overcome this problem.

BRIEF SUMMARY OF THE INVENTION

Disclosed herein are implants comprising a matrix, a pharmaceutical substance, and at least one excipient, wherein the pharmaceutical substance comprises a lipophilic moiety. The implants can be subcutaneous implants. In some embodiments, in an aqueous environment over a defined period of time, at least about 50% more of the pharmaceutical substance is released from an implant disclosed herein as is released from a comparable implant lacking the excipient. The defined period of time can be about 6 hours, about 24 hours, about 72 hours, or about 7 days. The aqueous environment can be selected from an aqueous solution, a sub-dermal location in a test animal, or a sub-dermal location in a human. The aqueous environment or aqueous solution can comprise an aqueous solution comprising about 137 mM NaCl, about 2.7 mM KCl, about 10 mM $Na_2HPO_4$, and about 1.8 mM $KH_2PO_4$ at about pH 7.4 and about 37° C.

In some embodiments, the excipient can comprise a compound selected from the group consisting of sugar alcohols and biodegradable polymers. In some embodiments, the excipient can comprises a compound selected from the group consisting of mannitol, glycerol, erythritol, threitol, arabitol, ribitol, xylitol, fucitol, galactitol, iditol, inositol, sorbitol, volemitol, isomalt, lactitol, and maltitol. In some embodiments, the excipient comprises mannitol. In some embodiments, the excipient comprises poly(lactic-co-glycolic) acid (PLGA).

In some embodiments, the lipophilic pharmaceutical substance comprises a lipid, such as a fatty acid, a monoglyceride, a diglyceride, a triglyceride, a phospholipid, and a steroid.

In some embodiments, the lipophilic pharmaceutical substance comprises a lipidated peptide.

In some embodiments, the lipophilic pharmaceutical substance comprises a fatty acid covalently conjugated to a peptide, such as liraglutide.

In some embodiments, the matrix of the implant comprises a non-biodegradable polymer, such as a polymer selected from the group consisting of ethylene vinyl acetate, polyolefins, polyethylenes, polypropylenes, polybutylenes, polyolefin copolymers, ethylene-methacrylic acid, ethylene-acrylic acid, vinyl aromatic polymers, polystyrene, vinyl aromatic copolymers, styrene-isobutylene copolymers, butadiene-styrene copolymers, polyvinyl alcohols, polyacetals, chloropolymers, polyvinyl chloride (PVC), fluoropolymers, polytetrafluoroethylene (PTFE), polyesters, polyethyleneterephthalate (PET), polyester-ethers, polyamides, nylon-6, nylon-6,6; polyethers, polyamide ethers, silicones, polyurethanes, polyurethane copolymers, polycarbonates, polycarbonate-based polyurethanes, and a mixture or copolymer of any of the foregoing. In some embodiments, the non-biodegradable polymer comprises ethylene vinyl acetate.

Also disclosed herein is an implant comprising a matrix, a pharmaceutical substance, and at least one excipient, wherein the pharmaceutical substance forms micelles in aqueous solution. In some embodiments, the aqueous solution is phosphate buffered saline (PBS) between about pH 7 and about pH 8.

Also disclosed herein is an implant comprising a matrix, a pharmaceutical substance, and at least one excipient, wherein the pharmaceutical substance is amphiphilic.

Also disclosed herein is an implant comprising a matrix, a pharmaceutical substance, and at least one excipient, wherein the pharmaceutical substance has been co-lyophilized with the excipient to form a pharmaceutical substance-excipient mixture prior to incorporation of the pharmaceutical substance-excipient mixture into the matrix. The pharmaceutical substance can be selected from the group consisting of a pharmaceutical substance which comprises a lipophilic moiety; a pharmaceutical substance which forms micelles in aqueous solution; and a pharmaceutical substance which is amphiphilic. In some embodiments, the pharmaceutical substance is liraglutide. In some embodiments, the excipient is a sugar alcohol, such as mannitol. In some embodiments, the excipient is poly(lactic-co-glycolic acid) (PLGA). In some embodiments, the matrix is ethylene vinyl acetate (EVA).

In any of the embodiments disclosed herein, the excipient: pharmaceutical substance ratio can range from about 5:1 to about 1:10 by weight, such as from about 1:1 to about 1:6 by weight.

In any of the embodiments disclosed herein, the weight ratio of matrix to (pharmaceutical substance+excipient) can range from about 10:1 to about 1:4, such as from about 5:1 to about 1:3.

Also disclosed herein is a subcutaneous implant comprising about 40% to about 60% by weight of ethylene vinyl acetate, and about 60% to about 40%% by weight of a mannitol:liraglutide mixture, wherein the mannitol:liraglutide mixture comprises about 10% to about 30% by weight mannitol and about 90% to about 70% by weight of liraglutide. The subcutaneous implant can comprise about 50% by weight of ethylene vinyl acetate, and about 50% by weight of a mannitol:liraglutide mixture, wherein the mannitol:liraglutide mixture comprises about 20% by weight mannitol and about 80% by weight of liraglutide.

In any of the embodiments disclosed herein, the implant can about 1 cm to about 5 cm long and about 1 mm to about 3 mm in diameter.

In any of the embodiments disclosed herein, the implant can be a subcutaneous implant.

In any of the embodiments disclosed herein, the implant can be prepared by hot melt extrusion.

In any of the embodiments disclosed herein, the implant can be dip-coated, for example, dip-coated with ethylene vinyl acetate. The dip-coating can be performed by dipping the implant into a 1% solution of EVA prepared in dichloromethane (DCM).

BRIEF DESCRIPTION OF THE DRAWINGS

FIG. 1 shows average liraglutide in vitro release from extrudates of 1.5 mm diameter×26 mm length, with an EVA dip-coated shell over a 50% EVA core formulation, expressed as % payload released.

DETAILED DESCRIPTION OF THE INVENTION

Disclosed herein are implants for long-term sustained drug delivery of lipophilic or amphiphilic pharmaceutical substances. In one embodiment, the implants have reduced burst release upon implantation. The implants comprise a matrix, a pharmaceutical substance, or multiple pharmaceutical substances, and at least one excipient, wherein the pharmaceutical substance comprises a lipophilic moiety, or, when multiple pharmaceutical substances are present, where at least one of the pharmaceutical substances comprises a lipophilic moiety, or where at least one of the pharmaceutical substances is amphiphilic. The pharmaceutical substance comprising a lipophilic moiety can comprise one lipophilic moiety, more than one lipophilic moiety, or the entire pharmaceutical substance may be considered as a lipophilic moiety (such as cholestane). The rate of release of the pharmaceutical substance or substances, total extent of release of the pharmaceutical substance or substances, or both the rate of release and the total extent of release of the pharmaceutical substance or substances from the implant, is increased by formulation of the implant together with the pharmaceutical substance or substances and the at least one excipient, as compared to the rate of release of the pharmaceutical substance or substances, total extent of release of the pharmaceutical substance or substances, or both the rate of release and the total extent of release of the pharmaceutical substance or substances from an implant formulated with the pharmaceutical substance or substances, but without the at least one excipient.

Definitions and General Descriptions

"Drug" and "pharmaceutical substance" are equivalent terms and are used interchangeably, and encompasses any substance intended for therapeutic, diagnostic, or nutritional use in a patient, individual, or subject in need thereof "Drugs" and "pharmaceutical substances" include, but are not limited to, diagnostic agents, therapeutic agents, hormones, nutrients, vitamins, and minerals.

A porogen is a first material which is embedded or mixed into a second material, which can be removed (for example, by dissolution, diffusion, or degradation) from the second material. The removal of the porogen results in the creation of pores in the second material.

"Biocompatible," when used to describe a material or system, indicates that the material or system does not provoke an adverse reaction, or causes only minimal, tolerable adverse reactions, when in contact with an organism, such as a human.

A "patient," "individual," or "subject" refers to a mammal, preferably a human, an agricultural animal such as a cow, pig, goat, or sheep, or a domestic animal such as a dog or cat. In a preferred embodiment, a patient, individual, or subject is a human.

"Treating" a disease or disorder with the implants and methods disclosed herein is defined as administering one or more of the implants disclosed herein to a patient in need thereof, with or without additional agents, in order to reduce or eliminate either the disease or disorder, or one or more symptoms of the disease or disorder, or to retard the progression of the disease or disorder or of one or more symptoms of the disease or disorder, or to reduce the severity of the disease or disorder or of one or more symptoms of the disease or disorder. "Suppression" of a disease or disorder with the implants and methods disclosed herein is defined as administering one or more of the implants disclosed herein to a patient in need thereof, with or without additional agents, in order to inhibit the clinical manifestation of the disease or disorder, or to inhibit the manifestation of adverse symptoms of the disease or disorder. The distinction between treatment and suppression is that treatment occurs after adverse symptoms of the disease or disorder are manifest in a patient, while suppression occurs before adverse symptoms of the disease or disorder are manifest in a patient. Suppression may be partial, substantially total, or total. Because some diseases or disorders are inherited, genetic screening can be used to identify patients at risk of the disease or disorder. The implants and methods as disclosed herein can then be used in asymptomatic patients at risk of developing the clinical symptoms of the disease or disorder, in order to suppress the appearance of any adverse symptoms.

"Therapeutic use" of the implants disclosed herein is defined as using one or more of the implants disclosed herein to treat a disease or disorder, as defined above. A "therapeutically effective amount" of a drug, a pharmaceutical substance, or a therapeutic agent is an amount of the drug, pharmaceutical substance, or agent, which, when administered to a patient, is sufficient to reduce or eliminate either a disease or disorder or one or more symptoms of a disease or disorder, or to retard the progression of a disease or disorder or of one or more symptoms of a disease or disorder, or to reduce the severity of a disease or disorder or of one or more symptoms of a disease or disorder. A therapeutically effective amount can be administered to a patient as a single dose, or can be divided and administered as multiple doses. In the context of implantable devices, a therapeutically effective amount describes an amount released from the implant which is sufficient to reduce or eliminate either a disease or disorder or one or more symptoms of a disease or disorder, or to retard the progression of a disease or disorder or of one or more symptoms of a disease or disorder, or to reduce the severity of a disease or disorder or of one or more symptoms of a disease or disorder. One or more implants can be used to deliver a therapeutically effective amount.

"Prophylactic use" of the implants disclosed herein is defined as using one or more of the implants disclosed herein to suppress a disease or disorder, as defined above. A "prophylactically effective amount" of a drug, pharmaceutical substance, or therapeutic agent is an amount of the drug, pharmaceutical substance, or agent, which, when administered to a patient, is sufficient to suppress the clinical manifestation of a disease or disorder, or to suppress the manifestation of adverse symptoms of a disease or disorder. A prophylactically effective amount can be administered to a patient as a single dose, or can be divided and administered as multiple doses. In the context of implantable devices, a prophylactically effective amount describes an amount released from the implant which is sufficient to reduce or eliminate either the disease or disorder, or one or more symptoms of the disease or disorder, or to retard the progression of the disease or disorder or of one or more symptoms of the disease or disorder, or to reduce the severity of the disease or disorder or of one or more symptoms of the disease or disorder. One or more implants can be used to deliver a prophylactically effective amount.

"Blood level" as used herein refers to the concentration of a drug, pharmaceutical substance, therapeutic agent, hormone, metabolite, or other substance in the blood of a subject. A blood level can be measured in whole blood, blood serum, or blood plasma, as per standard clinical laboratory practice for the substance to be assayed.

As used herein, the singular forms "a", "an", and "the" include plural references unless indicated otherwise or the context clearly dictates otherwise.

When numerical values are expressed herein using the term "about" or the term "approximately," it is understood that both the value specified, as well as values reasonably close to the value specified, are included. For example, the description "about 50° C." or "approximately 50° C." includes both the disclosure of 50° C. itself, as well as values close to 50° C. Thus, the phrases "about X" or "approximately X" include a description of the value X itself. If a range is indicated, such as "approximately 50° C. to 60° C." or "about 50° C. to 60° C.," it is understood that both the values specified by the endpoints are included, and that values close to each endpoint or both endpoints are included for each endpoint or both endpoints; that is, "approximately 50° C. to 60° C." (or "about 50° C. to 60° C.") is equivalent to reciting both "50° C. to 60° C." and "approximately 50° C. to approximately 60° C." (or "about 50° C. to 60° C.").

With respect to numerical ranges disclosed in the present description, any disclosed upper limit for a component or parameter may be combined with any disclosed lower limit for that component or parameter to provide a range (provided that the upper limit is greater than the lower limit with which it is to be combined). Each of these combinations of disclosed upper and lower limits are explicitly envisaged herein. For example, if ranges for the amount of a particular component or parameter are given as 10% to 30%, 10% to 12%, and 15% to 20%, the ranges 10% to 20% and 15% to 30% are also envisaged, whereas the combination of a 15% lower limit and a 12% upper limit is not possible and hence is not envisaged.

Unless otherwise specified, percentages of ingredients in compositions are expressed as weight percent, or weight/weight percent. It is understood that reference to relative weight percentages in a composition assumes that the combined total weight percentages of all components in the composition add up to 100. It is further understood that relative weight percentages of one or more components may be adjusted upwards or downwards such that the weight percent of the components in the composition combine to a total of 100, provided that the weight percent of any particular component does not fall outside the limits of the range specified for that component.

The partition coefficient P of a compound is defined as the ratio of the concentration of the compound in organic solvent to the concentration of the compound in water, in a biphasic mixture of organic solvent and water (where the organic solvent and water are not miscible). The base-10 logarithm of the partition coefficient, log P, is often used. Partition coefficients are often measured in octanol/water systems, and the partition coefficient in such a system is defined as:

$$P_{oct}=[\text{concentration in octanol}]\div[\text{concentration in water}].$$

For compounds which can ionize, the distribution coefficient D of a compound is defined as the ratio of the concentration of all species of the compound (ionized and unionized) in organic solvent to the concentration of all species of the compound (ionized and unionized) in water, in a biphasic mixture of organic solvent and water (where the organic solvent and water are not miscible). Log D may also be used. D will vary depending on the pH at which D is measured; preferably, D is measured at the physiological pH of 7.4. Distribution coefficients can be measured using octanol as the organic solvent. A solution of phosphate-buffered saline (PBS) at pH 7.4 can be used as the aqueous solvent when D is measured at physiological pH.

Some embodiments described herein are recited as "comprising" or "comprises" with respect to their various elements. In alternative embodiments, those elements can be recited with the transitional phrase "consisting essentially of" or "consists essentially of" as applied to those elements. In further alternative embodiments, those elements can be recited with the transitional phrase "consisting of" or "consists of" as applied to those elements. Thus, for example, if a composition or method is disclosed herein as comprising A and B, the alternative embodiment for that composition or method of "consisting essentially of A and B" and the alternative embodiment for that composition or method of "consisting of A and B" are also considered to have been disclosed herein. Likewise, embodiments recited as "consisting essentially of" or "consisting of" with respect to their various elements can also be recited as "comprising" as applied to those elements. Finally, embodiments recited as "consisting essentially of" with respect to their various elements can also be recited as "consisting of" as applied to those elements, and embodiments recited as "consisting of" with respect to their various elements can also be recited as "consisting essentially of" as applied to those elements.

When an implant, device, composition, or system is described as "consisting essentially of" the listed elements, the implant, device, composition, or system contains the elements expressly listed, and may contain other elements which do not materially affect the condition being treated (for compositions for treating conditions), or the properties of the described implant, device, or system. However, the implant, device, composition, or system either does not contain any other elements which do materially affect the condition being treated other than those elements expressly listed (for compositions for treating systems) or does not contain any other elements which do materially affect the properties of the implant, device, or system; or, if the implant, device, composition, or system does contain extra elements other than those listed which may materially affect the condition being treated or the properties of the system, the implant, device, composition or system does not contain a sufficient concentration or amount of those extra elements to materially affect the condition being treated by the composition or the properties of the implant, device, or system. When a method is described as "consisting essentially of" the listed steps, the method contains the steps listed, and may contain other steps that do not materially affect the condition being treated by the method or the properties of the implant, device, or system produced by or used by the method, but the method does not contain any other steps which materially affect the condition being treated by the method or the implant, device, or system produced or used other than those steps expressly listed.

This disclosure provides several embodiments. It is contemplated that any features from any embodiment can be combined with any features from any other embodiment where possible. In this fashion, hybrid configurations of the disclosed features are within the scope of the present disclosure.

Implant Structure and Manufacture

Physical Parameters of Implants as Disclosed Herein

In some embodiments, the implants disclosed herein are rod-shaped or generally rod-shaped, and are about 0.5 cm to 10 cm in length, such as from about 1 cm to about 6 cm in length, or from about 1 cm to about 5 cm in length, or about 1 cm to about 4 cm in length, or about 1 cm to 3 cm in length, or about 1.5 cm to 3.5 cm in length, or about 2 cm to 4 cm in length, or about 2 cm to about 3 cm in length, or about 2 cm to about 5 cm in length, or about 2 cm to about 6 cm in length, or about 3 cm to about 5 cm in length, or about 3 cm to about 6 cm in length, or about 4 cm to about 5 cm in length, or about 4 cm to about 6 cm in length, or about 2.6 cm in length. In some embodiments, the implants are rod-shaped or generally rod-shaped, and are about 3 cm to about 5 cm in length, or about 3.5 cm to about 4.5 cm, or about 4 cm. In some embodiments, the implants are rod-shaped or generally rod-shaped, and are about 5 cm to about 7 cm in length, or about 5.5 cm to about 6.5 cm, or about 6 cm.

In some embodiments, the implants are rod-shaped or generally rod-shaped, and are about 1 to about 3 mm in diameter. In some embodiments, the implants are rod-shaped or generally rod-shaped, and comprise dimensions of about 0.5 to about 7 mm in diameter, or about 2 to about 5 mm in diameter, or about 2 to about 3 mm in diameter, or about 2.4 mm in diameter, or about 3 mm in diameter.

Any of the recited lengths can be combined with any of the recited diameters. In some embodiments, the implants are rod-shaped or generally rod-shaped, and comprise dimensions of about 2.4 mm in total diameter and about 2.6 cm in total length.

Chemical Composition of Implants: Implant Matrix

The implants described herein can be formulated from any biocompatible substance that can be implanted into a subject, patient, or individual. The portion of the implant which serves as a carrier for the pharmaceutical substance, the excipient(s), and any other substances included in the implant, is referred to as the matrix or the matrix substance.

One such matrix is the polymer ethylene vinyl acetate (EVA). EVA is a copolymer of the monomers ethylene and vinyl acetate. The composition of EVA is usually specified as the percent by weight of vinyl acetate present, with the remaining percentage made up of ethylene. Various ratios of the monomers can be used, such as about 10% to about 50% vinyl acetate by weight, with the remainder being ethylene; about 20% to about 45% vinyl acetate; about 25% to about 40% vinyl acetate; about 30% to about 36% vinyl acetate, or about 33% vinyl acetate.

In some embodiments as disclosed herein, the implants additionally comprise a radiopaque substance. The radiopaque substance is preferably opaque to X-ray radiation. The radiopaque substance aids in precisely locating the implant in a non-invasive manner, for example, in an X-ray or CT scan. Barium salts, such as barium sulfate, are preferred radiopaque substances. Other radiopaque substances which can be used include, but are not limited to, zirconium oxide, bismuth oxide, bismuth salts, and tungsten compounds such as calcium tungstate.

In some embodiments as disclosed herein, the implants additionally comprise a substance which is detectable or identifiable by magnetic resonance imaging, for use in locating the implant during an MRI scan. Iron oxides, such as paramagnetic iron oxide ($Fe_3O_4$), can be used as a substance to visualize implants in an MRI scan.

In some embodiments as disclosed herein, the implants additionally comprise both a radiopaque substance and a substance which is detectable by magnetic resonance imaging.

The detectable substance or substances can be blended into the matrix of the implant if such blending does not substantially affect the pharmacokinetics of drug release. Alternatively, the detectable substance can be restricted to a particular location of the implant where it will not interfere with the pharmacokinetics of drug release, such as in the core of the implant, or at one or both end regions of the implant.

Pharmaceutical Substances and Drugs for Use in Implants

A variety of pharmaceutical substances and drugs can be used in the implants as disclosed herein.

Lipidated peptides: lipidated peptides (also referred to as lipopeptides) are peptides which have an attached lipid group. Lipidation of peptides can modulate the pharmacokinetic and pharmacodynamics properties of the peptide, such as by increasing their half-life in circulation, or by increasing the membrane permeability of the peptide. A lipidated peptide will have increased lipophilicity as compared to the unlipidated peptide. The implants disclosed herein can be used as drug delivery devices for lipidated peptides.

The attached lipid can comprise a fatty acid, a monoglyceride, a diglyceride, a triglyceride, a phospholipid, a steroid, or a combination of two or more of the foregoing lipids.

Liraglutide: the lipidated peptide liraglutide is an analog of glucagon-like peptide-1 (GLP-1), which has antihyperglycemic activity. Liraglutide differs from native human GLP-1 (7-37) by having an arginine residue instead of a lysine residue at position 34, and by having a C-16 fatty acid (palmitic acid) attached to the side chain of lysine-26 via a glutamic acid spacer. (Amino acid residue position numbers are those of GLP-1 (1-37), that is, 37-amino-acid long GLP-1; in liraglutide, the biologically active GLP-1 is truncated at the N-terminal and represents GLP-1 (7-37) with the additional modifications as described.) Liraglutide is typically administered subcutaneously. Liraglutide has a half-life of 11-15 hours, believed to be due to reversible binding to albumin, which prevents immediate degradation of the peptide.

Other lipidated peptides include echinocandins, capsofungin, surfactin, mycosubtilin, daptomycin, and pepducins.

Peptides derivatized with hydrophobic or lipophilic moieites: In addition to the lipids previously listed (a fatty acid, a monoglyceride, a diglyceride, a triglyceride, a phospholipid, a steroid, or a combination thereof), other lipophilic moieties can be attached to peptides for use in implants of the invention. These lipophilic moieties include eicosanoids, prostaglandins, thromboxanes, leukotrienes, resolvins, eoxins, lipoxins, sphingolipids, arachidonic acids, secosteroids, retinoids fat-soluble vitamins, vitamin D3, vitamin A, vitamin E, and vitamin K.

Proteolipids: proteins with one or more attached lipid moieties, such as myristoylated proteins (proteins with one or more attached myristic acid moieties) or palmitoylated proteins (proteins with one or more attached palmitic acid moieties) can be used in implants as disclosed herein.

Micelle-forming pharmaceutical substances and amphiphilic pharmaceutical substances: pharmaceutical substances which form micelles in aqueous solution can also be used in the implants. Micelle-forming substances are typically amphiphilic molecules, with a lipophilic portion and a hydrophilic portion. In aqueous solution, the molecules organize themselves into clusters with a roughly spherical arrangement, where the lipophilic portions point into the bulk of the spherical micelle (away from the aqueous solution), and the hydrophilic portions are on the surface of the spherical micelle, where they can interact with the aqueous solution.

Micelles can be lyophilized (freeze-dried) and re-constituted in aqueous solution. However, if lyophilized micelle powder is combined with a matrix and extruded under conditions for hot melt extrusion, the high temperature of extrusion will disrupt the micellar structure. Disruption of the micellar structure allows the lipophilic portion of the molecules to interact strongly with the matrix because the matrix material is typically hydrophobic, leading to poor elution of the amphiphilic pharmaceutical substance or micelle-forming pharmaceutical substance out of the matrix. Use of the excipients described herein with an amphiphilic pharmaceutical substance or a micelle-forming pharmaceutical substance is believed to stabilize and protect the micellar structure of the pharmaceutical substance during hot melt extrusion, which enhances the ability of the pharmaceutical substance to elute from the matrix of the implant.

Lipidated peptides (lipopeptides) often form micelles in aqueous solution, and it is believed that the mechanism described above provides for enhanced elution of lipidated peptides from the implants containing matrix, one or more lipidated peptides as pharmaceutical substance, and one or more excipients, as compared to elution of lipidated peptides from implants containing matrix and lipidated peptides, but without excipients.

Pharmaceutical substances and drugs for use in the implants may form micelles in a variety of aqueous solutions, such as one or more of distilled water, buffered water at pH between about 7 and about 8, phosphate buffered saline (PBS) between about pH 7 and about pH 8, or PBS at about pH 7.4.

Hydrophobic drugs and hydrophobic pharmaceutical substances:

Pharmaceutical Substances which are Relatively Hydrophobic can Also be Used in the Implants. Such substances typically have relatively high log P(oct) or log D(oct) values, such as at least about 2, at least about 3, or at least about 4 (representing a concentration in an octanol-water system which is at least about 100 times, at least about 1,000 times, or at least about 10,000 times higher in the octanol phase than in the water phase, respectively). Examples of such substances include iloprost (log Poct of about 4.8) and levothyroxine (log Poct of about 4) (values as reported by PubChem, URL pubchem.ncbi.nlm.nih.gov).

Excipients for Use in Implants

Excipients are used in the implants to provide for elution of the pharmaceutical substance from the implant matrix, which would either not occur in the absence of the excipient, which would occur at a slower rate in the absence of the excipient, or which would result in a lower total delivery of pharmaceutical substance over the lifetime of the implant. Examples of excipients that can be used are sugar alcohols and biodegradable polymers. Mixtures of any two or more of the excipients recited herein can also be used.

Sugar alcohols that can be used as excipients in the implants include mannitol, glycerol, erythritol, threitol, arabitol, ribitol, xylitol, fucitol, galactitol, iditol, inositol, sorbitol, volemitol, isomalt, lactitol, and maltitol. A subset of sugar alcohols that can be used includes the six-carbon compounds mannitol, fucitol, galactitol, iditol, inositol, and sorbitol. In one embodiment, mannitol is used as the excipient.

Biodegradable polymers that can be used as excipients in the implants include poly(lactic-co-glycolic acid) (PLGA). Other biodegradable polymers that can be used in the implants disclosed herein include biodegradable or bioerodible forms of polyamide, aliphatic polycarbonates, polyalkylcyanoacrylate, polyalkylene oxalates, polyanhydride, polycarboxylic acid, polyester, poly(hydroxybutyrate), polyimide, poly(iminocarbonate), polycaprolactone (PCL), poly-D,L-lactic acid (DL-PLA), polydioxanone, poly(glycolic acid), poly-L-lactic acid (L-PLA), poly-L-lactic acid-co-glycolic acid (PLGA), polyorthoester, polyphosphazenes, and polyphosphoester, poly(trimethylene carbonate), cellulose esters, and derivatives and mixtures thereof.

The excipient:drug ratio can range from about 5:1 to about 1:10 by weight, such as about 1:1 to about 1:6 (for example, about 1:1, about 1:2, about 1:3, about 1:4, about 1:5, or about 1:6), or about 1:3 to about 1:6. In one embodiment, the excipient:drug ratio is about 1:4.

The excipient can increase the amount of pharmaceutical substance released from the implant over a defined period of time in an aqueous environment. For example, at least about 20% more, at least about 30% more, at least about 40% more, at least about 50% more, at least about 60% more, at least about 70% more, at least about 80% more, at least about 90% more, or at least about 100% more of the pharmaceutical substance is released from the implant containing excipient as from a comparable implant lacking the excipient over a defined period of time. Alternatively, up to about 20% more, up to about 30% more, up to about 40% more, up to about 50% more, up to about 60% more, up to about 70% more, up to about 80% more, up to about 90% more, or up to about 100% more of the pharmaceutical substance is released from the implant containing excipient as from a comparable implant lacking the excipient over a defined period of time. The defined period of time can be about 30 minutes, about an hour, about two hours, about three hours, about four hours, about six hours, about 10 hours, about 12 hours, about 24 hours, about 48 hours, about 72 hours, about 4 days, about 5 days, about 6 days, about 7 days, about 10 days, about 14 days, about 20 days, about three weeks, about four weeks, about six weeks, about two months, about three months, about four months, about five months, or about six months. For in vitro testing purposes, measurement of comparative release from implants with excipient versus implants without excipient over defined periods of time between about six hours and about 7 days are preferred, such as 6 hours, 24 hours, 72 hours, or 7 days.

The aqueous environment in which comparative release is studied can be selected from water, an aqueous solution, a sub-dermal location in a test animal, or a sub-dermal location in a human. Test animals can be dogs, such as beagle dogs, pigs, apes, such as chimpanzees, or monkeys. The aqueous environment can be pure water, such as distilled water. Water used for the aqueous environment can be distilled water. For in vitro tests of comparative release, an aqueous solution of phosphate buffered saline (PBS) is preferred. The pH of the PBS can be between about pH 7 and about pH 8, such as about pH 7.4 to approximate physiological pH. The temperature of the PBS is preferably between about 35° C. to about 40° C., such as about 37° C. to approximate human body temperature. Samples for testing in PBS can be suspended in the PBS in wire baskets or other appropriate supports. The PBS can be stirred between about 20 RPM and about 100 RPM using a paddle or magnetic stir bar, such as at about 50 RPM. In one embodiment, the PBS comprises about 137 mM NaCl, about 2.7 mM KCl, about 10 mM $Na_2HPO_4$, and about 1.8 mM $KH_2PO_4$; preferably, the PBS is at about pH 7.4 and about 37 C.

Diseases Treatable with Implants as Disclosed Herein

The implants disclosed herein can be used in the treatment of diseases, by sustained and prolonged release of pharmaceutical substances from the implants once they are implanted into a subject or patient.

Liraglutide and related compounds are described in U.S. Pat. Nos. 6,268,343 and 8,846,618, which describe use of the compounds for methods of reducing blood glucose levels, treating diabetes type I, treating diabetes type II, treating impaired glucose tolerance, for glycemic control, treating obesity, reducing body weight, inhibiting gastric acid secretion, treating gastric ulcers, treating myocardial infarct, inhibiting apoptosis of β-cells, stimulating the proliferation of β-cells, treating dyslipidemia, treating stroke, treating left ventricular hypertrophy, treating arrhythmia, treating bacteraemia, treating septicaemia, treating irritable bowel disease, or treating functional dyspepsia.

Liraglutide (sold under the brand name VICTOZA® and SAXENDA®, which are trademarks of Novo Nordisk) is approved for use in the United States for the treatment of type 2 diabetes, particularly for glycemic control in subjects with type 2 diabetes; for treatment of obesity and to help obese or overweight subjects lose weight; and to reduce the risk of heart attack or stroke in subjects with type 2 diabetes.

In one embodiment, implants as disclosed herein comprising liraglutide and at least one excipient are used for methods of reducing blood glucose levels, treating diabetes type I, treating diabetes type II, treating impaired glucose tolerance, for glycemic control, treating obesity, reducing body weight, inhibiting gastric acid secretion, treating gastric ulcers, treating myocardial infarct, inhibiting apoptosis of β-cells, stimulating the proliferation of β-cells, treating dyslipidemia, treating stroke, treating left ventricular hypertrophy, treating arrhythmia, treating bacteremia, treating septicemia, treating irritable bowel disease, treating functional dyspepsia, to reduce the risk of heart attack or stroke, to reduce the risk of heart attack or stroke in subjects with diabetes, to reduce the risk of heart attack or stroke in subjects with type 1 diabetes, or to reduce the risk of heart attack or stroke in subjects with type 2 diabetes.

Exemplary Polymers for Use in Implants

A preferred polymer for use in the implants is ethylene vinyl acetate (EVA; poly(ethylene-co-vinyl acetate)). However, other biocompatible polymers can be used in the implants disclosed herein. As used herein, a "polymer" or "polymeric material" means a macromolecule comprising repeating monomer units or co-monomer units. The polymer may be a homopolymer, copolymer, terpolymer, or may contain more than three monomers.

Additional polymers that can be used in the implants disclosed herein include polyolefins, including polyethylenes, polypropylenes, and polybutylenes; polyolefin copolymers in addition to ethylene-vinyl acetate such as ethylene-methacrylic acid and ethylene-acrylic acid; vinyl aromatic polymers such as polystyrene; vinyl aromatic copolymers such as styrene-isobutylene copolymers and butadiene-styrene copolymers; polyvinyl alcohols; polyacetals; chloropolymers including polyvinyl chloride (PVC); fluoropolymers including polytetrafluoroethylene (PTFE); polyesters including polyethyleneterephthalate (PET); polyester-ethers; polyamides such as nylon 6 and nylon 6,6; polyethers; polyamide ethers; silicones; polyurethanes and polyurethane copolymers; polycarbonates; polycarbonate-based polyurethanes, and mixtures or copolymers of any of the foregoing.

The implants can comprise a single type of polymer or a mixture of two or more polymers. A mixture of two polymers may modulate the release rate of the drug. It is desirable that an effective therapeutic amount of the drug be released from any implant as disclosed herein for a reasonably long period of time. U.S. Pat. No. 6,258,121 to Yang et al. disclosed a method of altering the release rate by blending two polymers with differing release rates and incorporating them into a single layer; this technique can also aid in reducing burst release of drug upon implant.

The weight/weight ratio in the implant of matrix substance to combined pharmaceutical substance and excipient can range from about 10:1 of matrix/(pharmaceutical substance+excipient) to about 1:4 of matrix/(pharmaceutical substance+excipient), that is, from about 91% matrix and about 9% (pharmaceutical substance+excipient) to about 20% matrix and about 80% (pharmaceutical substance+excipient). In further embodiments, the ratio can range from about 5:1 matrix/(pharmaceutical substance+excipient) to about 1:3 matrix/(pharmaceutical substance+excipient); from about 3:1 matrix/(pharmaceutical substance+excipient) to about 1:3 matrix/(pharmaceutical substance+excipient); or from about 2:1 matrix/(pharmaceutical substance+excipient) to about 1:2 matrix/(pharmaceutical substance+excipient). In a further embodiment, the ratio is about 1:1 matrix/(pharmaceutical substance+excipient).

Porogenic Shell

In some embodiments, the implants can include a porogen-containing shell, which can further serve to regulate the release of drug from the implant. Implants comprising a porogen-containing shell are disclosed in International Patent Appl. WO 2018/067882, and the porogenic shells described therein can be applied to the implants described herein. A preferred polymer for the shell of the implants as disclosed herein is ethyl vinyl acetate (EVA). Other materials that can be used in a porogen-containing shell include polyolefins, including polyethylenes, polypropylenes, and polybutylenes; polyolefin copolymers in addition to ethylene-vinyl acetate such as ethylene-methacrylic acid and ethylene-acrylic acid; vinyl aromatic polymers such as polystyrene; vinyl aromatic copolymers such as styrene-isobutylene copolymers and butadiene-styrene copolymers; polyvinyl alcohols; polyacetals; chloropolymers including polyvinyl chloride (PVC); fluoropolymers including polytetrafluoroethylene (PTFE); polyesters including polyethyleneterephthalate (PET); polyester-ethers; polyamides such as nylon 6 and nylon 6,6; polyethers; polyamide ethers; silicones; polyurethanes and polyurethane copolymers; polycarbonates; polycarbonate-based polyurethanes, and mixtures or copolymers of any of the foregoing. In one embodiment, the porogen-containing shell comprises the same polymer which comprises the inner portion of the implant comprising the pharmaceutical substance and excipient. In one embodiment, the porogen-containing shell comprises a different polymer from the polymer which comprises the inner portion of the implant comprising the pharmaceutical substance and excipient.

Examples of porogens which can be used in the shell can include alkyl celluloses and hydroxyalkyl celluloses, such as ethylcellulose, methylcellulose, and hydroxymethylcellulose; fatty acids such as stearic acid, palmitic acid, myristic acid, and linoleic acid; biocompatible salts, such as sodium chloride, calcium chloride, or sodium phosphate; and soluble polymers such as low molecular weight polyvinylpyrrolidone (PVP). Porogen particles are preferably used in a tight size distribution to enable control over the size of the pores. The mean diameter of the porogens used can be between about 1 micrometer and about 300 micrometers. In some embodiments, the mean diameter of the porogens is greater than the thickness of the shell. In some embodiments, the mean diameter of the porogens is about equal to the thickness of the shell. In some embodiments, the mean diameter of the porogens is less than the thickness of the shell. In some embodiments, the mean diameter of the porogens is less than about 75% of the thickness of the shell. In some embodiments, the mean diameter of the porogens is less than about 50% of the thickness of the shell. In some embodiments, the mean diameter of the porogens is less than about 25% of the thickness of the shell.

A single material can be used as the porogen used in the shell. Alternatively, two or more different porogen materials can be used.

Porogens can be removed from the implant shell prior to implantation. In other embodiments, the implant can be implanted without removing the porogens; the porogens can then dissolve after implantation.

Implant Coating

The implants as disclosed herein can optionally be coated partially or entirely with a coating to control drug release. Implants can be dip-coated, spray-coated, pan-coated, or coated in a fluidized bed system. The coating can be applied by co-extrusion when implants are made by extrusion methods.

Rod-shaped implants can have a coating applied to their entire surface, followed by cutting small portions of the ends of each rod. This results in a partially coated rod, where the planar surfaces at each end of the rod have drug-containing matrix exposed, while the curved cylindrical sides are coated. If the coating is applied to the curved cylindrical sides by co-extrusion, cutting the extruded rod into pieces to form individual implant swill expose drug-containing matrix at each end of the rod.

The coating can be impermeable to the drug, in which case the coating should only partially cover the implant in order for drug to be released from the uncoated portion of the implant, or the coating should dissolve or degrade after a period of time to allow drug to be released from the newly-exposed drug-containing matrix. Alternatively, the coating can be permeable to the drug to a greater or lesser extent, allowing modulation of drug release.

The implants can be dip-coated with ethylene vinyl acetate. Dip-coating with ethylene vinyl acetate can be performed by dipping the implant into a solution (such as a 1% solution) of ethylene vinyl acetate into dichloromethane. The implant can be dipped once, or can be dipped multiple times (for example, two, three, or four times, or more if a thicker coating is desired).

Manufacture of Implants as Disclosed Herein

In some embodiments, the implants as disclosed herein can be produced by blending fine particles of polymer with particles of pharmaceutical substance of the desired size and co-extruding the blend. The blend mixture is heated to a temperature suitable for extrusion, such as the softening point of the polymer. At this point, optionally and if necessary, the softened mixture can be homogenized. The mixture is then co-extruded, e.g., via Microtruder screw extruder, Model No. RCP-025, Randcastle Extrusion Systems, Cedar Grove, NJ, or via other extrusion devices known in the industry. The diameter of extrusion, as well as temperature, pressure and other parameters can be controlled as appropriate for each polymer and pharmaceutical substance.

The extrudate can be extruded horizontally and collected for further processing. The extrudate can be cut into desirable lengths, e.g., from about 1 to about 3 cm. The extrudate can then washed with or immersed in a solvent or solvents which remove any excess drug from the surface of the implant. Examples of solvents which can be used for washing the extrudate include water, saline, aqueous buffers, and alcohols such as ethanol or isopropanol. Mixtures of water and alcohols can also be used, such as ethanol-water mixtures. Preferable solvents are 100% ethanol or water-ethanol mixtures. For implants which use a porogenic shell, the implants can be washed with a solvent which removes the porogen from the shell if removal of porogen prior to implantation is desired.

Washing of the extrudate may be followed by drying to remove wash solvent. Drying is typically done between about 30° C. and about 60° C. for about 6 to about 24 hours, such as at about 40° C. for about 12 hours.

Drying may be followed by packaging and sterilization. Implants may be vacuum-packed in moisture barrier foil pouches, heat-sealed and/or vacuum-sealed, and then sterilized using gamma irradiation, such as about 20 to 30 kilograys, or about 25 kilograys, or about 2.5 to about 3.5 Megarad, or about 2.9 to about 3.1 Mrads, or about 3 Mrads.

Liraglutide Implants

Also described herein are implants containing liraglutide suitable for use in subjects, individuals, or patients. The liraglutide implants are comprised of:

- a matrix comprising ethylene vinyl acetate (EVA), wherein the EVA comprises about 10% to about 50% vinyl acetate by weight, with the remainder being ethylene; about 20% to about 45% vinyl acetate; about 25% to about 40% vinyl acetate; about 30% to about 36% vinyl acetate, or about 33% vinyl acetate;
- a pharmaceutical substance comprising liraglutide or a pharmaceutically acceptable salt thereof; and
- an excipient comprising a sugar alcohol or a biodegradable polymer.

The EVA in the liraglutide implant is preferably about 33% vinyl acetate.

The excipient:liraglutide ratio can range from about 5:1 to about 1:10 by weight, about 1:1 to about 1:6, or about 1:3 to about 1:6. In a preferred embodiment, the excipient:drug ratio is about 1:4.

The excipient is preferably mannitol or poly(lactic-co-glycolic acid) (PLGA), more preferably mannitol. The weight ratio of matrix to (pharmaceutical substance+excipient) ranges from about 10:1 to about 1:4, about 5:1 to about 1:3, about 3:1 to about 1:3, preferably about 2:1 to about 1:2, or more preferably about 1:1.

In some embodiments, the liraglutide implants are rod-shaped or generally rod-shaped. In some embodiments, the liraglutide implants and are about 0.5 cm to 10 cm in length, such as from about 1 cm to about 6 cm in length, or from about 1 cm to about 5 cm in length, or about 1 cm to about 4 cm in length, or about 1 cm to 3 cm in length, or about 1.5 cm to 3.5 cm in length, or about 2 cm to 4 cm in length, or about 2 cm to about 3 cm in length. In some embodiments, the liraglutide implants are about 1 to about 3 mm in diameter. In some embodiments, the implants are about 0.5 to about 7 mm in diameter, or about 2 to about 5 mm in diameter, or about 2 to about 3 mm in diameter, or about 2.4 mm in diameter, or about 3 mm in diameter. In some embodiments, the liraglutide implants are about 2.4 mm in total diameter and about 2.6 cm in total length.

Pharmacological Properties of Implants

Pharmacokinetics

The implants can provide an approximately constant blood level of pharmaceutical substance or drug. The level of drug delivery should be within the therapeutic range of the drug, and lower than a level that causes unacceptable toxicity. In one embodiment, implants as disclosed herein can comprise multiple drugs. In one embodiment, more than one implant may be inserted into a patient, where the implants contain the same drug, to achieve a desired level of drug concentration in the blood. In one embodiment, more than one implant may be inserted into a patient, where the implants contain different drugs, to achieve a desired level of drug concentration in the blood for each of the different drugs.

Implants as disclosed herein may be designed to provide a steady-state concentration of drug in the blood (e.g., in plasma or serum). Implants as disclosed herein may be designed such that the resulting concentration of drug in the blood remains essentially constant over extended periods of time. Implants as disclosed herein may be designed such that the resulting concentration of drug in the blood remains approximately constant over extended periods of time.

The release of drug from the implants as disclosed herein is dependent on the rate of dissolution of drug in the matrix, on passive diffusion of drug through the polymer matrix, on diffusion of drug through any optional coating, and on other parameters.

Drug release rates are also affected by washing of the implant prior to insertion into the patient. The implants may be washed with a solvent such as water, ethanol, isopropanol, etc., which can help reduce burst release upon initial implantation of the implant.

An "approximately constant blood level" refers to an approximately constant level of drug over a period of time in the blood of the subject or patient. As previously defined, "blood level" refers to the concentration of a drug, hormone, metabolite, or other substance in the blood of a subject, and can be measured in whole blood, blood serum, or blood plasma, as per standard clinical laboratory practice for the substance to be assayed. In one embodiment, an approximately constant blood level of drug varies by no more than about ±30% over a day, over a week, over a month, over three months, over six months, or over nine months, as compared to the mean or average blood level over that time period. In another embodiment, an approximately constant level of drug varies by no more than about ±20% over a day, over a week, over a month, over three months, over six months, or over nine months, as compared to the mean or average blood level over that time period. In another embodiment, an approximately constant level of drug varies by no more than about ±10% over a day, over a week, over a month, over three months, over six months, or over nine months, as compared to the mean or average blood level over that time period. An "approximately constant release rate" indicates that an approximately constant amount of the pharmaceutical substance is released from an implant as disclosed herein over a period of time, such as over a day, over a week, over a month, over three months, over six months, or over nine months. In some embodiments, the approximately constant release rate varies by no more than about ±50%, about ±40%, about ±30%, about ±20%, or about ±10% over the time period indicated, as compared to the average or mean release. An approximately constant release rate is preferred in order to achieve an approximately constant blood level. By "essentially constant" is meant that for about 95% of the extended period of time, the concentration of drug in blood is within about three, about two, or preferably about one standard deviation of the mean blood level. Measurements of the blood level can be performed hourly, twice a day, daily, twice a week, weekly, every two weeks, monthly, or at any other periodic interval for determination of the mean blood levels. For example, if the mean blood level of a drug sampled at weekly intervals is 2.0 ng/ml, and one standard deviation of the measurement is ±0.1 ng/ml, then blood levels that fall within about ±0.3 ng/ml, about ±0.2 ng/ml, or preferably about ±0.1 ng/ml for about 95% of the measurements are considered essentially constant. By "extended periods of time" is meant from a period of about 3 months to a period of about 1 year, or longer, e.g., an extended period of time can be about 3 months or at least about 3 months, about 4 months or at least about 4 months, about 5 months or at least about 5 months, about 6 months or at least about 6 months, about 9 months or at least about 9 months, about 12 months or at least about 12 months, about 15 months or at least about 15 months, about 18 months or at least about 18 months, about 21 months or at least about 21 months, about 24 months or at least about 24 months, or more than about 24 months.

Insertion and Removal of Implants

Another aspect of this disclosure is a method for delivering a pharmaceutical substance or drug to a patient in need thereof, comprising the step of inserting an implant or implants as disclosed herein into the patient, wherein the pharmaceutical substance or drug is released from the implant or implants into the patient. In a preferred method of this disclosure, implants as disclosed herein are administered by subdermal implantation. In various embodiments, the implants are subdermally implanted at a site selected from a group consisting of the upper arm, scapular region, the back, the leg and the abdomen. Before implantation, the patient may be lightly anesthetized, e.g., with isoflurane or other anesthetic known in the art, and/or may have topical, transdermal, or subdermal anesthetic applied at the site of implantation. A small incision can be made through the skin and a trocar inserted subdermally, then loaded with one implant. The stylet can be inserted to hold the implant in place and the trocar carefully removed, leaving the implant in the subdermal space. Each site can be sutured closed and examined later. Complications such as skin irritation, inflammation, infection or other site-specific adverse effects can be monitored and treated, e.g., with antibiotics, as needed.

In various embodiments, implants as disclosed herein can be left in the body for up to about one year, about two years, or longer. The implants can be left in the body for up to about 3 months, up to about 6 months, up to about 9 months, up to about 12 months, up to about 15 months, up to about 18 months, up to about 21 months, or up to about 24 months or longer. The period of sustained release of drug into the body is thus from about 1 month to about 1 year, or longer, or from about 3 months to about 1 year or longer, e.g., at least about 3 months, at least about 6 months, at least about 9 months, at least about 12 months, at least about 15 months, at least about 18 months, at least about 21 months, or at least about 24 months or longer. In some embodiments the implants can be left in the body for more than 1 year. Implants may be removed from the body at the end of the treatment period, through an incision, e.g., a 3-mm incision, using forceps.

A second implant may, for example, be used to deliver a pharmaceutical substance to counteract any adverse effects caused by a drug released from a first implant.

Multiple implants may be inserted into a single patient to regulate the delivery of a single drug, or to deliver several drugs.

EXEMPLARY EMBODIMENTS

The invention is further described by the following embodiments. The features of each of the embodiments are combinable with any of the other embodiments where appropriate and practical.

Embodiment 1

An implant comprising a matrix, a pharmaceutical substance, and at least one excipient, wherein the pharmaceutical substance comprises a lipophilic moiety.

Embodiment 2

The implant of embodiment 1, wherein the implant is a subcutaneous implant.

Embodiment 3

The implant of embodiment 1, wherein in an aqueous environment over a defined period of time, at least about 50% more of the pharmaceutical substance is released from the implant as is released from a comparable implant lacking the excipient.

Embodiment 4

The implant of embodiment 3, wherein the defined period of time is about 6 hours, about 24 hours, about 72 hours, or about 7 days.

Embodiment 5

The implant of embodiment 3 or embodiment 4, wherein the aqueous environment is selected from an aqueous solution, a sub-dermal location in a test animal, or a sub-dermal location in a human.

Embodiment 6

The implant of embodiment 3 or embodiment 4, wherein the aqueous environment comprises an aqueous solution comprising about 137 mM NaCl, about 2.7 mM KCl, about 10 mM $Na_2HPO_4$, and about 1.8 mM $KH_2PO_4$ at about pH 7.4 and about 37° C.

Embodiment 7

The implant of any one of embodiments 1-4, wherein the excipient comprises a compound selected from the group consisting of sugar alcohols and biodegradable polymers.

Embodiment 8

The implant of any one of embodiments 1-7, wherein the excipient comprises a compound selected from the group consisting of sugar alcohols.

Embodiment 9

The implant of any one of embodiments 1-7, wherein the excipient comprises a compound selected from the group consisting of mannitol, glycerol, erythritol, threitol, arabitol, ribitol, xylitol, fucitol, galactitol, iditol, inositol, sorbitol, volemitol, isomalt, lactitol, and maltitol.

Embodiment 10

The implant of any one of embodiments 1-7, wherein the excipient comprises mannitol.

Embodiment 11

The implant of any one of embodiments 1-7, wherein the excipient comprises a compound selected from the group consisting of biodegradable polymers.

Embodiment 12

The implant of any one of embodiments 1-7, wherein the excipient comprises poly(lactic-co-glycolic) acid (PLGA).

Embodiment 13

The implant of embodiment 1, wherein the lipophilic pharmaceutical substance comprises a lipid.

Embodiment 14

The implant of embodiment 13, wherein the lipid is selected from the group consisting of a fatty acid, a monoglyceride, a diglyceride, a triglyceride, a phospholipid, and a steroid.

Embodiment 15

The implant of embodiment 1, wherein the lipophilic pharmaceutical substance comprises a lipidated peptide.

Embodiment 16

The implant of embodiment 1, wherein the lipophilic pharmaceutical substance comprises a fatty acid.

Embodiment 17

The implant of embodiment 1, wherein the lipophilic pharmaceutical substance comprises a fatty acid covalently conjugated to a peptide.

Embodiment 18

The implant of embodiment 17, wherein the lipophilic pharmaceutical substance comprising a fatty acid covalently conjugated to a peptide comprises liraglutide.

Embodiment 19

The implant of embodiment 1, wherein the matrix comprises a non-biodegradable polymer.

Embodiment 20

The implant of embodiment 19, wherein the non-biodegradable polymer comprises a polymer selected from the group consisting of: ethylene vinyl acetate, polyolefins, polyethylenes, polypropylenes, polybutylenes, polyolefin copolymers, ethylene-methacrylic acid, ethylene-acrylic acid, vinyl aromatic polymers, polystyrene, vinyl aromatic copolymers, styrene-isobutylene copolymers, butadiene-styrene copolymers, polyvinyl alcohols, polyacetals, chloropolymers, polyvinyl chloride (PVC), fluoropolymers, polytetrafluoroethylene (PTFE), polyesters, polyethyleneterephthalate (PET), polyester-ethers, polyamides, nylon-6, nylon-6,6; polyethers, polyamide ethers, silicones, polyurethanes, polyurethane copolymers, polycarbonates, polycarbonate-based polyurethanes, and a mixture or copolymer of any of the foregoing.

Embodiment 21

The implant of embodiment 19, wherein the non-biodegradable polymer comprises ethylene vinyl acetate.

Embodiment 22

An implant comprising a matrix, a pharmaceutical substance, and at least one excipient, wherein the pharmaceutical substance forms micelles in aqueous solution.

Embodiment 23

The implant of embodiment 22, wherein the aqueous solution is phosphate buffered saline (PBS) between about pH 7 and about pH 8.

Embodiment 24

An implant comprising a matrix, a pharmaceutical substance, and at least one excipient, wherein the pharmaceutical substance is amphiphilic.

EXAMPLES

The following examples are intended to illustrate the invention, and are not intended to limit the invention to the embodiments exemplified.

Example 1

Preparation of Liraglutide-EVA Test Samples

Liraglutide without excipient: liraglutide (Auro Peptides) was used as the active pharmaceutical ingredient (API). A mild, buffered, endotoxin-free base solution (ammonium bicarbonate, pH=7.4, filtered through 0.2 μm PTFE membrane) was prepared for treatment of the API. API (0.53 g) was dissolved in 100 mL of the base solution and lyophilized in two equal aliquots. Following lyophilization, the removal of ammonium bicarbonate solids was incomplete. The sample was neutralized with excess acetic acid, dried, redissolved in $NH_4OH$ solution (pH=9.0), and lyophilized again to yield the final product.

Liraglutide-poly(lactide-co-glycolide) (liraglutide-PLGA) mixture: 100 mg API was suspended in 5 mL solution of 100 mg PLGA (50/50) in dichloromethane/acetone (1:1 by volume). The suspension was then added dropwise to pyrogen-free water while homogenizing with a hand-held rotor-stator mixer. The resulting emulsion was stirred overnight to evaporate the remaining solvent and then lyophilized to obtain a dry powder.

Liraglutide-mannitol mixture: a stock solution of 0.4 M mannitol (Aldrich) was prepared. An aliquot containing an estimated 1.001 g of mannitol was then combined with 100 mL basified liraglutide solution ($NH_4OH$, pH=8.5) containing 5.007 g of the active substance. The resulting transparent solution was lyophilized to yield a dry powder weighing 5.975 g and containing 83.3% w/w liraglutide.

Extrusion Methods: API was blended with cryomilled EVA powder and extruded. Extrusions were performed using a Thermo Scientific Haake Minilab micro-compounding machine Type 557 2200, equipped with co-rotating screws and a force feeder. The extruder screws were Therma Pharma MiniHME Screws and the barrel plates were corrosion-resistant R&D parts used for clamshell assembly. The barrel temperature was set to 80° C., and the respective powder blends were hand-loaded into the force feeder auger. The screw torque was set to a fixed level of 50 N·cm, and the products were extruded through a 1.5 mm nozzle. Extruded rods were approximately 26 mm long and 1.5 mm in diameter.

Pellet pressing: pellets were pressed to simulate the hot-melt process on a smaller scale than is possible using extrusion methods. 100 mg portion of each of the dried powders (liraglutide without excipient, liraglutide-PLGA, and liraglutide-mannitol) as prepared above, was manually blended with 100 mg cryomilled EVA resin (lot ENG-EVA-B060816). The 200 mg powder blend was then pressed into five (5) individual pellets, weighing approximately 40 mg each, using a hydraulic press and pellet die warmed to 80° C. The pellets were then compared for their respective in vitro release characteristics.

Example 2

In Vitro Release and Analysis

Extruded rods and pellets were tested for in vitro release in bottles set in a shaking water bath. The media was 100 mL of pH 7.4 phosphate buffered saline, kept at 37° C. and 50 RPM. Rods and pellets were wrapped in wire sinkers. Samples were taken at 6 hours and 24 hours; at each time point 100 uL was withdrawn and replaced with fresh media.

Liraglutide content was analyzed via HPLC using a Supelco Discovery C18 column (150×4.6 mm, 5 um), with mobile phase composed of 20 mM potassium phosphate buffer (pH 8.0) combined with acetonitrile at a ratio of 85:15 (v:v), and a flow rate of 1.0 mL/min. The column temperature was 40° C. and detection was measured at 214 nm, with a 20 uL injection volume and a run time of 20 minutes. Standards were prepared in pH 8.0 phosphate buffer.

Compounded specimens (API-EVA mixtures) were compared with a reference standard for the API as well as a control sample consisting of a powder blend of the API with cryomilled EVA. Sample portions were placed into small vials and dissolved with 2 mL of DCM, then allowed to sit overnight until dissolved. Then 0.1 mL of the dissolved solution was sampled with a positive displacement pipette and diluted up to 10 mL in pH 8.0 phosphate buffer. Solutions were mixed well and a volume of approximately 1 mL was micro centrifuged and analyzed by HPLC.

Example 3

In Vitro Release of Liraglutide API Without Excipient

Liraglutide was blended with cryomilled EVA powder and extruded as described above, with a drug loading of 50% (w/w). Average recovery of the API/EVA powder blend, sampled for in vitro release before being fed into the extruder, was 94% w/w. After extrusion into rods 26 mm long and 1.5 mm in diameter, in vitro recovery of API from the rods varied from 14% to 20%.

Example 4

Comparative In Vitro Release of Liraglutide API with and Without Excipient

Pellets were prepared as described in Example 1, containing liraglutide without excipient, liraglutide with mannitol excipient, and liraglutide with PLGA excipient. In vitro release was tested as described in Example 2. The results are shown in Table 1.

TABLE 1

| Sample Added to EVA | Theoretical Loading of Blend with EVA (w/w) | Measured Drug Content (w/w) (±1 s.d.) | Extraction Efficiency |
|---|---|---|---|
| As-Received API | 50% | 21.1 ± 5.0% | 42 ± 10% |
| Lyophilized API (pH = 9) | 50% | 16.7 ± 5.6% | 33 ± 11% |
| Lyophilized API with 20% Mannitol (pH = 8.5) | 40% | 27.7 ± 4.2% | 69 ± 10% |
| PLGA-Encapsulated API | 25% | 18.9 ± 11.3% | 76 ± 45% |

Example 5

In Vitro Release of Liraglutide with Mannitol Excipient from Extruded Rods

Extruded rods were prepared as described above with the liraglutide-mannitol mixture and EVA. Molten material recovered from the extruder barrels was tested for payload (n=3), yielding a measured drug content of 39.9±2.8% by weight from a theoretical loading of 42%. Tested extrudate samples (n=3) yielded an average API content of 50.4±1.5%.

In vitro measurement of liraglutide release from the extruded rods showed an average release of 38.7±2.6% after 24 hours. Dip coating of the rods was thus investigated in order to modulate the release rate.

Example 6

In Vitro Release of Liraglutide with Mannitol Excipient from Extruded, Dip-Coated Rods Extruded rods with the liraglutide-mannitol mixture were overcoated with EVA resin by dipping into a 1% solution of EVA prepared in dichloromethane (DCM). Samples were individually dipped three times each and dried in between. The average drug load for the dip-coated specimens (n=3) was 50.3±1.4%. The dip-coated ends of each sample were cut away prior to testing, to mimic a cut core/shell co-extrusion with open ends. FIG. 1 shows the amount of drug released as a percentage of load over time, up to 72 hours.

Although the foregoing invention has been described in some detail by way of illustration and examples for purposes of clarity of understanding, it will be apparent to those skilled in the art that certain changes and modifications may be practiced without departing from the spirit and scope of the invention. Therefore, the description should not be construed as limiting the scope of the invention.

All publications, patents, and patent applications cited herein are hereby incorporated by reference in their entirety.

What is claimed is:

1. An implant comprising a non-biodegradable matrix, and a mixture of a lipophilic pharmaceutical substance and at least one excipient, the mixture dispersed in the matrix, wherein the matrix includes a non-biodegradable polymer, wherein the lipophilic pharmaceutical substance comprises a lipid conjugated to a pharmaceutical substance, wherein the at least one excipient includes a sugar alcohol, and wherein the implant is generally rod-shaped.

2. The implant of claim 1, wherein the implant is a subcutaneous implant.

3. The implant of claim 1, wherein in an aqueous environment over a defined period of time, at least about 50% more of the pharmaceutical substance is released from the implant as is released from a comparable implant lacking the excipient.

4. The implant of claim 3, wherein the defined period of time is about 6 hours, about 24 hours, about 72 hours, or about 7 days.

5. The implant of claim 3, wherein the aqueous environment is selected from an aqueous solution, a sub-dermal location in a test animal, or a sub-dermal location in a human.

6. The implant of claim 3, wherein the aqueous environment comprises an aqueous solution comprising about 137 mM NaCl, about 2.7 mM KCl, about 10 mM $Na_2HPO_4$, and about 1.8 mM $KH_2PO_4$ at about pH 7.4 and about 37° C.

7. The implant of claim 1, wherein the sugar alcohol is the only excipient present in the implant.

8. The implant of claim 1, wherein the sugar alcohol comprises one or more of mannitol, glycerol, erythritol, threitol, arabitol, ribitol, xylitol, fucitol, galactitol, iditol, inositol, sorbitol, volemitol, isomalt, lactitol, and maltitol.

9. The implant of claim 8, wherein the sugar alcohol comprises mannitol.

10. The implant of claim 1, wherein the lipid is selected from the group consisting of a monoglyceride, a diglyceride, a triglyceride, a phospholipid, and a steroid.

11. The implant of claim 1, wherein the lipophilic pharmaceutical substance comprises a lipidated peptide.

12. The implant of claim 1, wherein the lipid conjugated to a pharmaceutical substance is formed from conjugation of the pharmaceutical substance with a fatty acid.

13. The implant of claim 1, wherein the lipophilic pharmaceutical substance comprises a fatty acid covalently conjugated to a peptide.

14. The implant of claim 13, wherein the lipophilic pharmaceutical substance comprising a fatty acid covalently conjugated to a peptide comprises a lipidated peptide comprising a glucagon-like peptide 1 analog.

15. The implant of claim 1, wherein the non-biodegradable polymer comprises a polymer which does not substantially degrade in a subdermal space of a mammal, said polymer selected from the group consisting of: ethylene vinyl acetate, polyolefins, polyethylenes, polypropylenes, polybutylenes, polyolefin copolymers, ethylene-methacrylic acid, ethylene-acrylic acid, vinyl aromatic polymers, polystyrene, vinyl aromatic copolymers, styrene-isobutylene copolymers, butadiene-styrene copolymers, polyvinyl alcohols, polyacetals, chloropolymers, polyvinyl chloride (PVC), fluoropolymers, polytetrafluoroethylene (PTFE), polyesters, polyethyleneterephthalate (PET), polyester-ethers, polyamides, nylon-6, nylon-6,6; polyethers, polyamide ethers, silicones, polyurethanes, polyurethane copolymers, polycarbonates, polycarbonate-based polyurethanes, or a mixture or copolymer of any of the foregoing.

16. The implant of claim 1, wherein the non-biodegradable polymer comprises ethylene vinyl acetate.

17. The implant of claim 1, wherein the excipient:lipophilic pharmaceutical substance ratio ranges from about 5:1 to about 1:10 by weight.

18. The implant of claim 17, wherein the excipient: lipophilic pharmaceutical substance ratio ranges from about 1:1 to about 1:6 by weight.

19. The implant of claim 1, wherein the weight ratio of matrix to (lipophilic pharmaceutical substance+excipient) ranges from about 10:1 to about 1:4.

20. The implant of claim 19, wherein the weight ratio of matrix to (lipophilic pharmaceutical substance+excipient) ranges from about 5:1 to about 1:3.

21. The implant of claim 1, wherein the implant is about 1 cm to about 5 cm long and about 1 mm to about 3 mm in diameter.

22. The implant of claim 1, wherein the implant is prepared by hot melt extrusion.

23. The implant of claim 1, wherein the implant is dip-coated.

24. The implant of claim 23, wherein the implant is dip-coated with ethylene vinyl acetate.

25. The implant of claim 23, wherein the implant is dip-coated with ethylene vinyl acetate by dipping the implant into a 1% solution of EVA prepared in dichloromethane (DCM).

26. The implant of claim 14 wherein the lipidated peptide includes liraglutide.

27. An implant comprising a non-biodegradable matrix, and a mixture of a lipophilic pharmaceutical substance and at least one excipient, the mixture dispersed in the matrix, wherein the matrix includes a non-biodegradable polymer, wherein the at least one excipient includes a sugar alcohol, wherein the lipophilic pharmaceutical substance, when present in saline, forms micelles of the lipophilic pharmaceutical substance, and wherein the implant is substantially generally rod-shaped.

28. The implant of claim 27, wherein the saline is phosphate buffered saline (PBS) between about pH 7 and about pH 8.

29. An implant comprising a non-biodegradable matrix, and a mixture of an amphiphilic pharmaceutical substance and at least one excipient, the mixture dispersed in the matrix, wherein the matrix includes a non-biodegradable polymer, wherein the at least one excipient includes a sugar alcohol, and wherein the implant is generally rod-shaped.

30. The implant of claim 29, wherein the amphiphilic pharmaceutical substance includes a lipidated peptide comprising a glucagon-like peptide 1 analog.

31. The implant of claim 29, wherein the sugar alcohol is the only excipient present in the implant.

32. The implant of claim 29, wherein the sugar alcohol includes mannitol.

33. The implant of claim 29, wherein the matrix includes ethylene vinyl acetate (EVA).

34. The implant of claim 30, wherein the lipidated peptide includes liraglutide.

35. A subcutaneous implant comprising:

about 40% to about 60% by weight of a non-biodegradable matrix including ethylene vinyl acetate, and about 60% to about 40% by weight of a mixture of mannitol and a lipidated peptide comprising a glucagon-like peptide 1 analog, wherein said mixture comprises about 10% to about 30% by weight mannitol and about 90% to about 70% by weight of lipidated peptide, and wherein the implant is generally rod-shaped.

36. The subcutaneous implant of claim 35, comprising:

about 50% by weight of ethylene vinyl acetate, and about 50% by weight of the mixture of mannitol and a lipidated peptide comprising a glucagon-like peptide 1 analog, wherein said mixture comprises about 20% by weight mannitol and about 80% by weight of lipidated peptide.

37. The implant of claim 35, wherein the lipidated peptide includes liraglutide.

38. The implant of claim 37, wherein the lipidated peptide is liraglutide.

* * * * *